United States Patent [19]

Courtois

[11] Patent Number: 5,972,889
[45] Date of Patent: *Oct. 26, 1999

[54] METHOD FOR INHIBITING THE PROLIFERATION OF EPITHELIAL LENS CELLS AND IMPLANTABLE LENS THEREFOR

[75] Inventor: Yves Courtois, Boulogne-Billancourt, France

[73] Assignee: Pharmacia S.p.A., Milan, Italy

[ * ] Notice: This patent is subject to a terminal disclaimer.

[21] Appl. No.: 08/979,129

[22] Filed: Nov. 26, 1997

Related U.S. Application Data

[63] Continuation of application No. 08/290,788, filed as application No. PCT/EP93/00389, Feb. 18, 1993, Pat. No. 5,843,893.

[30] Foreign Application Priority Data

Feb. 19, 1992 [GB] United Kingdom ................... 9203533

[51] Int. Cl.⁶ ............................. A61K 38/00; C07K 1/00; A61F 13/00
[52] U.S. Cl. ................................... 514/12; 514/8; 514/21; 514/912; 530/399; 530/402; 530/409; 530/410; 530/849; 424/78.04; 424/422
[58] Field of Search ................................... 514/12, 8, 21, 514/912; 530/399, 402, 409, 410, 849; 424/78.04, 422

[56] References Cited

FOREIGN PATENT DOCUMENTS

WO 90/12597 11/1990 WIPO.

Primary Examiner—Cecilia J. Tsang
Assistant Examiner—Abdel A. Mohamed
Attorney, Agent, or Firm—Seed and Berry LLP

[57] ABSTRACT

A conjugate of a polypeptide reactive with a fibroblast growth factor receptor and a cytotoxic agent is used for inhibiting the proliferation of epithelial lens cells, especially following extracapsular cataract surgery.

14 Claims, 8 Drawing Sheets

METHOD FOR INHIBITING THE PROLIFERATION OF EPITHELIAL LENS CELLS AND IMPLANTABLE LENS THEREFOR

CROSS-REFERENCE TO RELATED APPLICATIONS

This application is a continuation of U.S. patent application Ser. No. 08/290,788, filed Oct. 12, 1994, now U.S. Pat. No. 5,843,893; which was filed under 35 U.S.C. Title 35, §371 from PCT Application No. PCT/EP93/00389, filed Feb. 18, 1993; which was based on Great Britain Application No. 9203533.6, filed Feb. 19, 1992.

TECHNICAL FIELD

This invention relates to uses of a conjugate comprising a cytotoxic agent and a polypeptide reactive with a fibroblast growth factor (FGF) receptor.

BACKGROUND OF THE INVENTION

The FGF family currently consists of seven members. The most widely studied molecules to date, acidic and basic FGF (aFGF and bFGF), are two structurally related polypeptides of molecular weight 15000–18000 kD. They were isolated originally from bovine brain, pituitary and retinal tissues but are also present in many other tissues. Basic FGF is a mitogenic factor for most cells of mesodermal and ectodermal origin via binding to specific cell surface receptors. Indeed, high and low affinity binding sites for bFGF have been identified in baby hamster kidney (BHK) cells and many other cell types including bovine lens epithelial cells (BEL cells). Basic FGF also binds to basement membranes in a dose dependent manner probably on the polysaccharide part of the heparan sulfate proteoglycans.

Recent studies have established the feasibility of conferring cytotoxic activities to bFGF by chemically conjugating potential toxins to the growth factor. As an example, saporin is a ribosome inactivating protein isolated from *Saponaria officinalis* which can be chemically conjugated to bFGF. The resulting bFGF-saporin conjugate (bFGF-SAP) is a specific cytotoxin for cells expressing the bFGF receptor (Lappi et al., Biochem. Biophys. Res. Commun. 160: 2, 917–923, 1989; Lappi et al, J. Cell. Physiol. 147, 17–26, 1991). Because the coupling between saporin and bFGF does not affect bFGF affinity for heparin or its high affinity receptor, the conjugate has all the characteristics of the mitogen. WO 90/125597 discloses conjugates comprising a cytotoxic agent and a polypeptide reactive with a FGF receptor, for example bFGF-SAP, for use in treating FGF-mediated pathophysiological conditions such as tumours, atherosclerosis, rheumatoid arthritis and proliferative retinopathy.

The present invention, however, is concerned with the treatment of another pathological condition. This condition is a side-effect of cataract surgery, in particular cataract surgery performed by a technique which leaves the posterior part of the lens capsule in place. The purpose of leaving in place the posterior part of the lens capsule is to maintain the vitreous fluid at its place in the eye and, most of the time, to anchor the lens implant.

In many instances, the lens cells which are left at the periphery migrate and divide. They then occupy the center of the lens capsule and impair vision. This can occur in about 30% of cases within several months in young patients or within a year in old patients. New surgery or laser treatment is needed to break the membrane that forms, which is costly and not harmless.

We have found that a bFGF-SAP conjugate is bound tightly to a lens capsule. The presence of the conjugate prevents the migration and proliferation of epithelial lens cells. Other eye tissue, such as the corneal endothelium which controls corneal transparency, is not damaged. These findings have general applicability.

SUMMARY OF THE INVENTION

Accordingly, the present invention provides use of a conjugate comprising a cytotoxic agent and a polypeptide reactive with a PGF receptor in the preparation of a medicament for use in inhibiting the proliferation of epithelial lens cells. In this way, the growth of residual lens epithelial cells, which are known to migrate and proliferate on the posterior lens capsule after extracapsular cataract surgery, may be interrupted to prevent secondary opacification of the capsule.

DETAILED DESCRIPTION OF THE INVENTION

Suitable conjugates are described in WO 90/12597. The polypeptide reactive with a FGF receptor is typically a FGF such as aFGF, bFGF or other proteins exhibiting bFGF mitogenic activity mediated through binding to a FGF receptor. A test for such activity is the ability to stimulate proliferation of cultured bovine aortic endothelial cells (Gospodarowicz et al, J. Biol. Chem. 257, 12266–12278, 1982; Gospodarowicz et al, PNAS USA 73, 4120–4124, 1976).

The FGF may be a human FGF produced by recombinant DNA techniques or derived from natural sources or a mammalian FGF, eg. a bovine, murine or rodent FGF. FGF also includes chemically modified FGF such as a FGF in which at least one of the four cysteine aminoacid residues are derivatized. A FGF may therefore be a carboxymethylated FGF wherein the —SH group of one or more of the cysteine residues has been converted into a —S—$CH_2$—COOH group. Any bFGF molecule as described in, for instance, WO 86/07595; WO 87/01728; EP-A-0226181; Abraham et al, EMBO J. 5, 2523–2528, 1986; or Lobb, Eur. J. Clin. Invest. 18, 321–336, 1988; may be usefully employed.

A mixture of bFGFs may be employed. This may be an approximately 50:50 mixture of:

a 154 amino acid human bFGF having the amino acid sequence of the 155 amino acid form which is reported by Abraham et al but without the N-terminal Met residue; and a 153 amino acid human bFGF having the amino acid sequence reported in Abraham et al but without the N-terminal Met and Ala residues.

Human basic FGF, for example produced by recombinant DNA techniques, is preferred for use in the present invention. A specific carboxymethylated FGF for use in the invention is the 146 amino acid form of bFGF, as described in WO 87/01728, wherein the two cysteine residues at positions 69 and 87 are irreversibly blocked by carboxymethyl groups, i.e. as —S—$CH_2$—COOH groups.

The cytotoxic agent may be an agent which inhibits protein synthesis. The agent may be a ribosome-inactivating protein (RIP), for example a type 1 RIP. The RIP may be a saporin such as saporin-6. other cytotoxic agents which may be used are ricin, ricin A chain, gelonin, diphtheria toxin, diphtheria toxin A chain, Pseudomonas exotoxin and drugs such as an methotrexate or an anthracycline glycoside such as doxorubicin, daunorubicin, idarubicin or epirubicin.

The polypeptide reactive with a FGF receptor can be conjugated to the cytotoxic agent by means known to those skilled in the art, such as through derivitization with a reactive sulfhydryl-containing moiety such as N-succinimidyl-3(2-pyridyldithio)propionate (SPDP) or via a cross-linking agent such as glutaraldehyde or carbodiimide. In one embodiment, the cytotoxic agent is derivatized with a reactive sulfhydryl-containing agent, such as SPDP. The polypeptide reactive with a FGF receptor is then added to and mixed with the derivatized cytotoxic agent. The resulting conjugate can be separated from the unreacted products on a column. A preferred conjugate which can be formed in this way is a FGF-saporin conjugate, for example a bFGP-saporin conjugate such as a bFGF-(saporin-6) conjugate.

Alternatively, the polypeptide reactive with a FGF receptor can be conjugated to a drug, such as 14-bromo-doxorubicin through the sugar moiety, as by the cisaconitate method (Shen and Riser, BBRC 102, 1048, 1981). Where the cytotoxic agent is a polypeptide, conjugates can be prepared by recombinant methods. Such methods as applied to conjugates of interleukin-2 (IL-2) or TGFα are provided in Chaudhary et al, Proc. Natl. Acad. Sci. USA 84, 4538–4542, 1987 and Lorberman-Galski et al, Proc. Natl. Acad. Sci. USA 85, 1922–1926, 1988. See also Maniatis, et al, Molecular Cloning: A Laboratory Manual, Cold Spring Harbor laboratory (1982).

The conjugates are used to inhibit the proliferation of epithelial lens cells in the eye of a patient, for example a human patient. They may therefore inhibit the proliferation after extracapsular cataract surgery of the epithelial lens cells. Preferably, however, the corneal endothelium of the eye should be intact. A therapeutically effective amount of the conjugate may be administered to a patient in need of it.

A conjugate may be administered directly into the eye during cataract surgery. Once the anterior part of the lens and nucleus have been removed, the conjugate may be injected before closure of the eye. A dose of from 50 to 1000 nM of the conjugate, for example of from 100 to 500 nM, may be injected into the human eye. The injection is typically into the anterior chamber of the eye. The conjugate may be injected in from 50 to 200, for example 100, $\mu$l of a suitable solution.

The conjugates may be formulated into a pharmaceutical composition, therefore, also comprising a pharmaceutically acceptable carrier or diluent. An agent for use in inhibiting the proliferation of epithelial lens cells can therefore be provided. The composition may be formulated for local application to the posterior lens capsule. The conjugate may be provided in solution in Water for Injections or physiological saline.

Alternatively, the conjugate may be formulated with a product used during cataract surgery for preventing damage of the corneal endothelium. A suitable product is hyaluronic acid, which is sold under the trade name HEALON™. Other products capable of stabilising a conjugate due to the presence of polyanion charges may be used.

A lens implant may be provided as part of the cataract surgery. The conjugate may be provided on the surface of the implant. Such a lens implant also forms part of the invention. A lens implant may therefore be inserted within an empty lens capsule. The implant may be coated with the conjugate. This may be achieved by soaking the implant in a solution, typically an aqueous solution of the conjugate. The implant may be pre-coated with heparin the facilitate binding of the conjugate to the implant.

The following Examples illustrate the invention. In the accompanying drawings:

BRIEF DESCRIPTION OF THE DRAWINGS

FIG. 8 shows the immunolocalization of bFGF-SAP on BEL cell cultures using a rabbit polyclonal antibody against saporin.

EXAMPLE 1

MATERIAL AND METHODS

Reagents

Figure 1A:
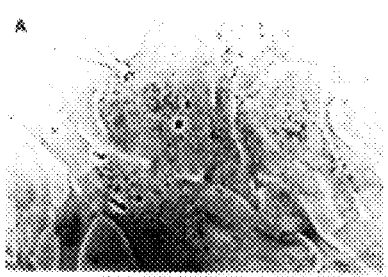
FIG. 1 shows the effect of bFGF-SAP conjugate on BEL cell morphology after a 4 day incubation (FIG 1A: control, FIG. 1B: cells treated with 10 nM saporin alone, FIG. 1C: cells treated with 0.01 nM bFGF-SAP, FIG. 1D: cells treated with 0.1 nM bFGF-SAP, FIG 1E: cells treated with 1 nM bFGF-SAP, FIG. 1F: cells treated with 10 nM bFGF-SAP). The arrow indicates cell debris. X102.
Figure 1B:
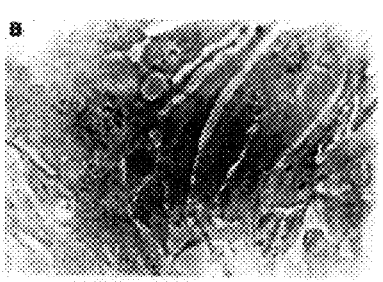
Figure 1C:
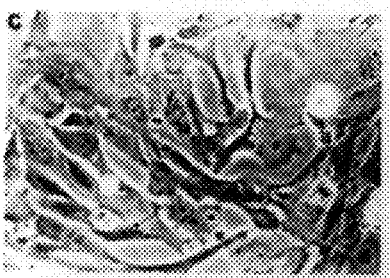
Figure 1D:
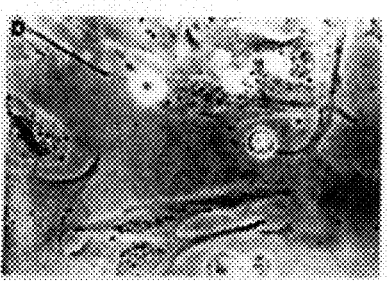
Figure 1E:
Figure 1F:

Saporin and bFGF-SAP were prepared as previously described (Lappi et al, Biochem. Biophys. Res. Commun. 129, 3, 934–942, 1985; Lappi et al, 1989). Recombinant bFGF was a generous gift of Farmitalia Carlo Erba (Italy). Polyclonal anti-saporin antibodies were generated in rabbits as described (Lappi et al, 1985) and anti-fibronectin antibodies were purchased from Collaborative Research (Mass., USA), anti-rabbit Ig biotinylated antibodies from Amersham France, F.I.T.C-extravidin from Sigma (France).

Cell culture

Bovine epithelial lens cells (BEL cells) were prepared as previously described (Hughes et al, Eur. J. Biochem. 52, 143–155, 1975) and maintained at 37° C. in Eagle's minimum essential medium containing 6% fetal calf serum (MEM 6% FCS), 50 µg/ml gentamycin, 25 µg/ml amphotericin B and 10 mg/ml glutamine in an atmosphere of 5% $CO_2$ and 95% air. The cells were subcultered at a ratio of 1:2.

Extracellular matrix preparation

Extracellular matrix (ECM) was produced by bovine corneal endothelial cells ($5^{th}$ passage) grown in the presence of bFGF. A few days after they reached confluence, the cells were removed by hypotonic treatment (with cold, bidistilled water) for 30 mn. The remaining nuclei and cytoskeletons were removed by a 2–3 mn exposure to 0.025N $NH_4OH$ (V lodavsky et al, Exp. Cell. RRs. 14, 149–159, 1982) and the underlying ECM was rinsed several times with bidistilled water, followed by 6 washings with 2M Nacl in order to remove as much bFGF as possible (Moscatelli, J. Cell. Biol. 107, 753–759, 1988). The dishes were then again washed several times with bidistilled water.

Posterior lens capsules preparation

Posterior lens capsules (PLC) were obtained by dissection of lenses of freshly killed animals and gently spread in 35 mm Petri dishes after having been washed in bidistilled water.

In Vitro effects of bFGF-SAP

BEL cells at the eighth passage were plated in 24 wells tissue culture plates containing MEM 6% FCS (10,000 cells per well). The following day, the medium was removed and cells in triplicate wells were then exposed to either medium alone, bFGF, saporin, an equimolor mixture of non conjugated bFGF and saporin or bFGF-SAP diluted in MEM 6% FCT at various concentrations. The growth of the cells and their morphology were monitored with a Leitz inverted microscope. Four days later, the cells were washed twice, trypsinized and the cell number determined with a Coulter particle counter. BEL cells were grown to confluency after having been seeded at the same density in 35 mm Petri dishes and submitted to the above treatment.

In order to establish the effects of bFGF biding on the matrix and on basement membrane, 35 mm dishes coated with the prepared ECM or with lens posterior capsules were filled with either distilled water, bFGF, bFGF-SAP or saporin diluted in bidistilled water at the concentrations of 100 nM or 20 nM. One hour later, the media were removed and the dishes washed.several times with distilled water. The following day, BEL cells were seeded at low density (20,000 cells per dish). Thereafter, the medium was changed to very 3 to 4 days. Morphological changes were studied with a Leitz inverted microscope. Cells in dishes coated with ECM were counted 10 days later.

Time course of bFGF-SAP action

BEL cells were prepared as described above, but were seeded at a density of $2.10^4$ cells per well. The following day, the medium was removed from the wells and the cells were exposed for 15 mn, 30 mn, 1 h, 3 h or 24 h to medium containing 1 nM bFGF-SAP. After treatment, the wells were three times with phosphate buffered saline (PBS) and filled with 1 ml of MEM 6% of FCS. The cells were counted four days after the first exposure to bFGF-SAP.

Immunolocalization of saporin

Some cultures grown on coverslips were exposed to 10 nM bFGF-SAP in HEM 6% FCS, for either 15 mn, 30 mn, 1 h, 3 h, 24 h or 48 h. Immediately following exposure, they were then fixed for 30 mn at room temperature with 1% paraformaldehyde in PBS. Other cultures were exposed to 10 nM bFGF-SAP for 15 mn, after which the medium was removed, the wells washes 3 times with PBS, and filled with MEM 6% FCS. These BEL cells were then fixed after either 15 mn, 30 mn, 1 h, 3 h, 24h or 48 h of incubation.

Cells were permeabilized by treatment with 0.1% Triton X 100 in PBS for 2 mn, and incubated for 30 mn at room temperature-with anti-saporin antibodies at 1/500 dilution. Non specific binding was reduced by pre-incubation with 5% goat serum in PBS. Immune complexes were revalued by successive incubations with biotinylated anti-rabbit Ig antibody and FITC-extravidin. A non immune rabbit serum was used as a control. Cells were photographed with a Zeiss photomicroscope using 400 ASA Ilford films.

RESULTS

Modulation of BEL cell Droliferation by bFGF-SAP

Figure 2:
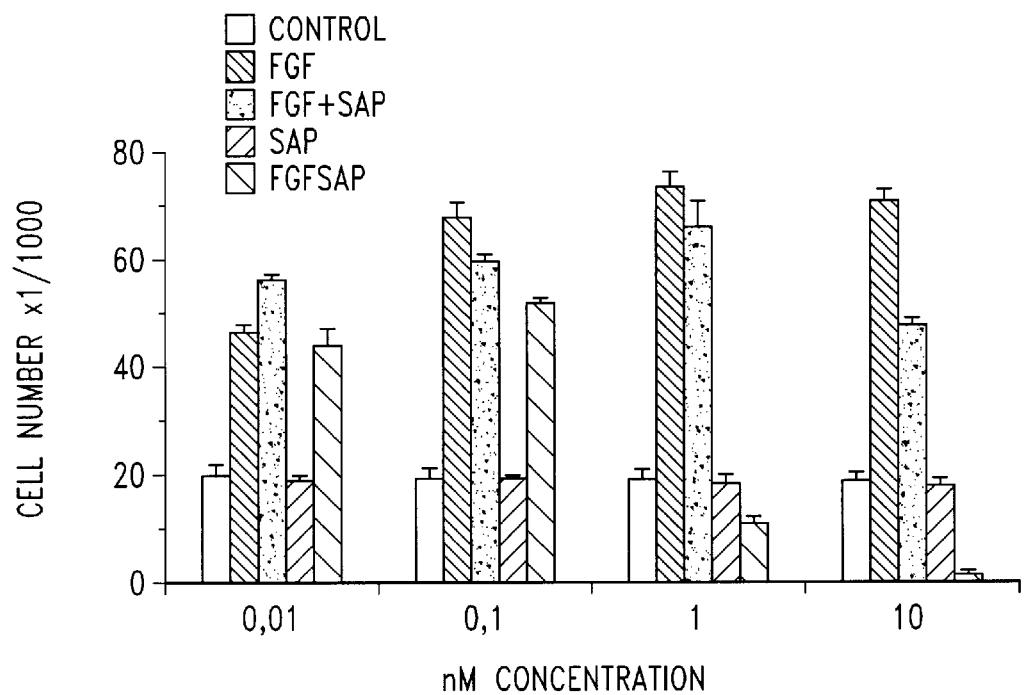
FIG. 2 shows the effect of bFGF, saporin, bFGF-SAP and of an equimolar mixture of non-conjugated bFGF and saporin on the proliferation of BEL cells seeded in 24 wells plates (10000 cells per well). The cells were seeded 24 hours before the beginning of the exposure. The cells were counted after a 4 day exposure (mean of triplicate experiments).

The morphology of BEL cells treated as described in methods for 4 days is shown in FIG. 1. Without exogenous FGF, BEL cells grow slowly and appear as large, rounded cells. Upon treatment with bFGF and bFGF-SAP at all concentrations, the cells became thinner and elongated, and divide faster than controls. However, with a 1 nM treatment of bFGF-SAP, obvious sings of toxicity (vacuoles in the cytoplasmes and in the nucleus) are observed. With a 10 nM bFGF-SAP treatment, only a few spare cells remain alive after a four day of incubation. Morphological signs of toxicity occur after 48 to 72 hours. The effect is specific for the conjugate because, at these doses, saporin alone had not toxic effect on BEL cells (FIG. 2). Moreover, the presence of saporin does not interfere with the cellular response to bFGF. As shown in FIG. 2, we observed a biphasic effect of FGF-SAP with increasing concentrations to 0.1 nM stimulating proliferation and, at higher doses, cell toxicity. This effect may reflect increased sensitivity to the basis FGF component of the conjugate over that the saporin.

Figure 3:
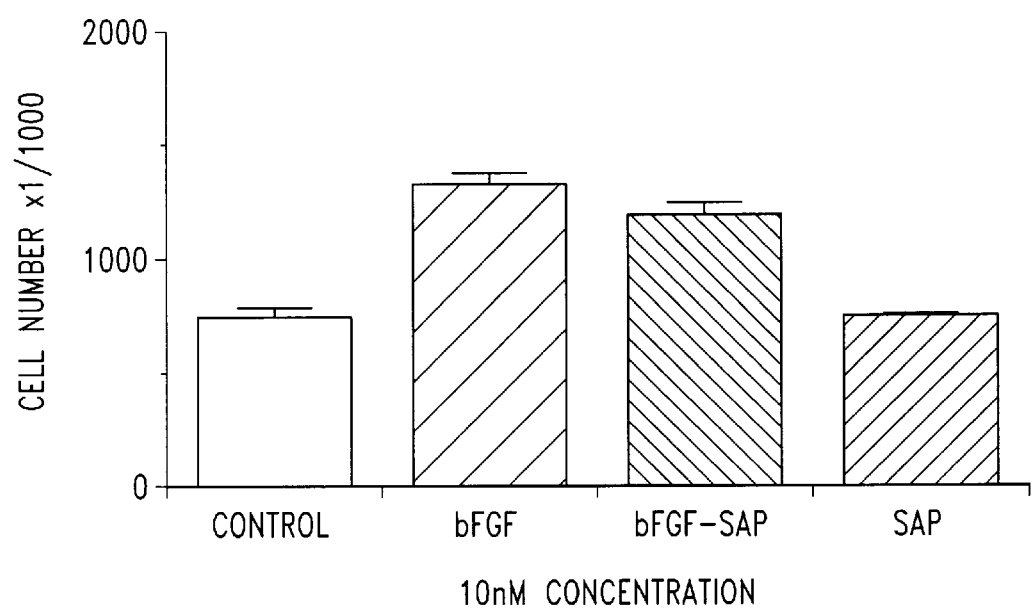
FIG. 3 shows the effect of 10 nM bFGF, bFGF-SAP, and saporin on confluent BEL cells growth. BEL cells were grown to confluency after having been seeded in 35 mm Petri dishes (100,000 cells per dish). The cells were counted after a 4 day incubation (mean of triplicate experiments).
Figure 4A:
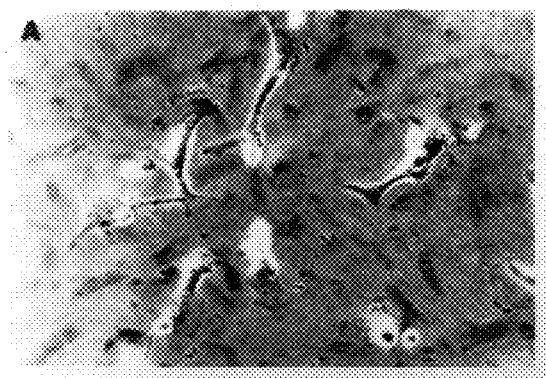
FIG. 4 shows the effect of pretreating extracellular matrix (ECM) with bFGF, saporin and bFGF-SAP on BEL cell morphology. The photographs were taken 10 days after the cells were seeded at low density (20,000 cells per dish). Cells grown on 100 nM bFGF-SAP pretreated ECM FIG. 4A, on 100 nM bFGF pretreated ECM FIG. 4B, on 100 nM saporin pretreated ECM FIG. 4C. Cells grown on non-pretreated ECM FIG. 4D. X85.
Figure 4B:
Figure 4C:
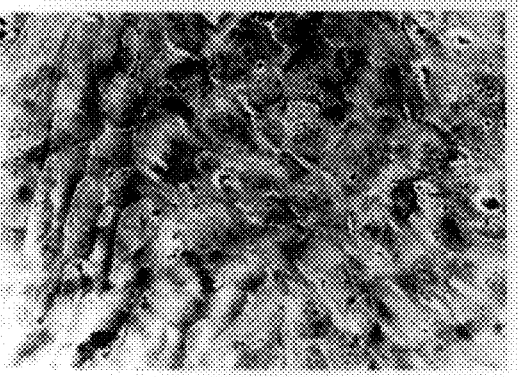
Figure 4D:
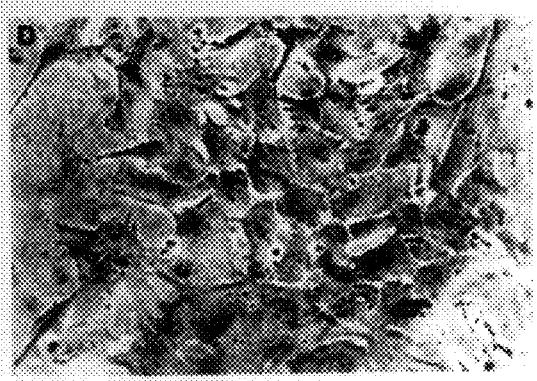

As shown in FIG. 3, the results were guite different when this experiment was repeated on cells grown to confluency. The 10 nM bFGF-SAP, which had an extremely toxic effect on exponential cells, had a positive proliferative effect on confluent cells, only slightly inferior to the one observed with bFGF.

Figures 5A, 5B, 5C, 5D, 5E, 5F:
FIG. 5 shows the effect of pretreating posterior lens capsule with 100 nM FGF, saporin, and FGF-SAP on BEL cell morphology. Very few elongated cells grow on the lens capsule that is pre-incubated with 100 nM FGF-SAP FIGS. 5A, 5B, and 5C). Cells grown on the plastic Petri dish (P.D.) become elongated and more widely spaced upon contact with the lens capsule (L.C.). Cells grown on the lens capsules that were pre-incubated with bFGF had the same morphology than cells stimulated by bFGF in vitro and accumulated on the capsules FIG. 5D. Pre-incubation of the capsules with saporin alone did not change the cellular morphology FIG. 5E compared to control cells FIG. 5F. X57.
Figure 6A:
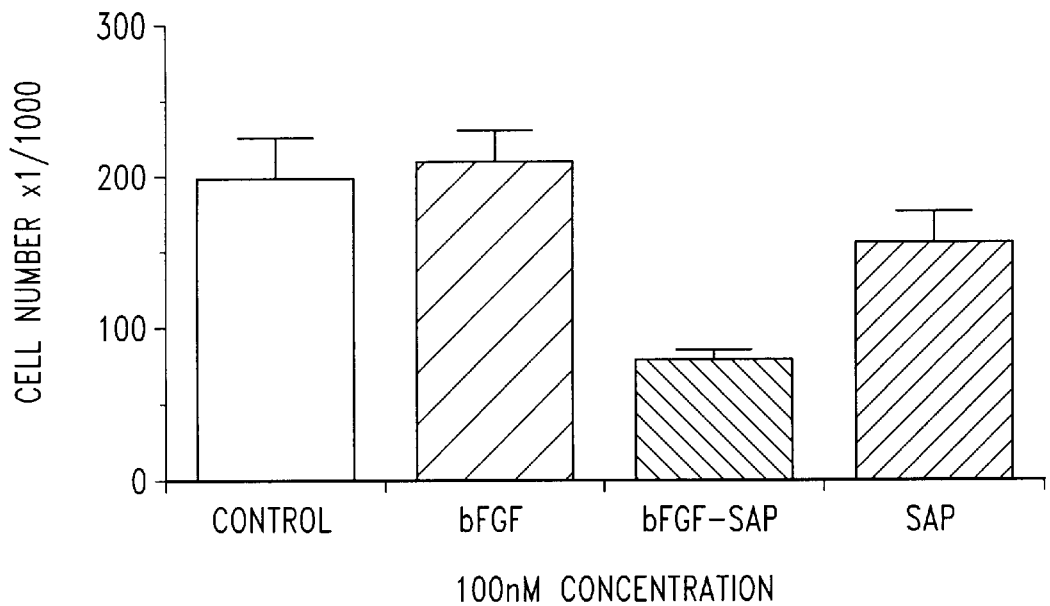
FIG. 6a shows the effect of pre-incubating extracellular matrix with 100 nM bFGF, bFGF-SAP, and saporin on BEL cell proliferation. Thirty five mm Petri dishes coated with ECM were filled during 1 hour with either 100 nM bFGF, bFGF-SAP, or saporin diluted to bidistilled water, then washed several times with bidistilled water. The following day, BEL cells were seeded at low density (20,000 cells per dish). The cell number was determined after a 10 day incubation (mean of three experiments).
Figure 6B:
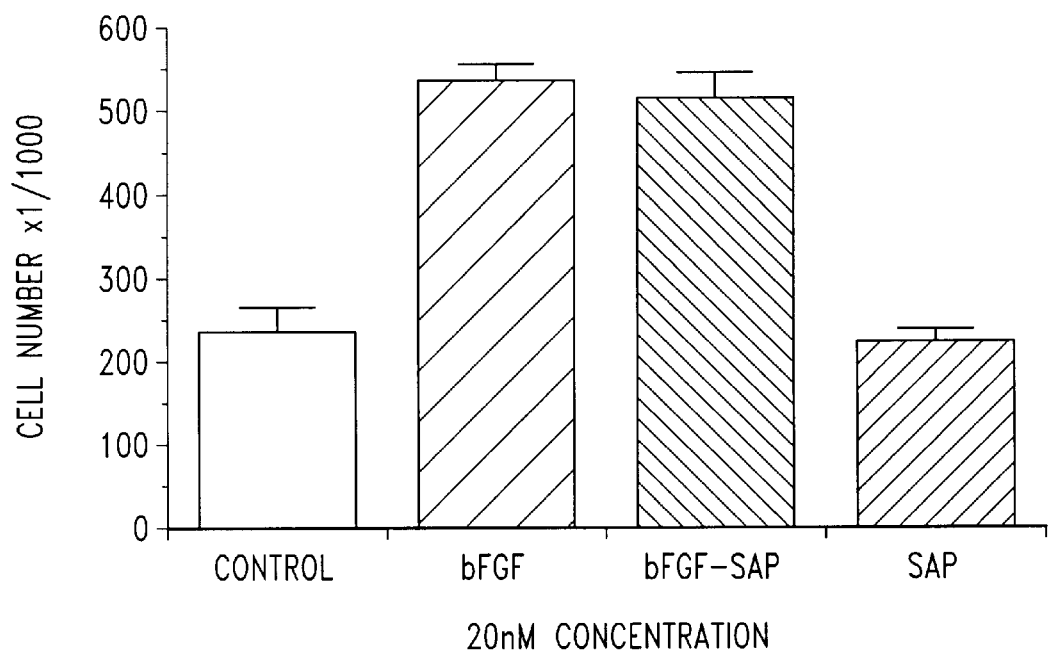
FIG. 6b shows the effect of pre-incubating extracellular matrix with 20 nM bFGF, bFGF-SAP, and saporin on BEL cell proliferation. The cell number was determined after a 10 day incubation (mean of three experiments).

Effect of pre-incubation of ECM and posterior lens capsule with bFGF-SAP on BEL cells proliferation BEL cells grown on either pretreated matrix or on posterior lens capsules exhibited the same morphological changes (FIGS. 4 and 5) as described above for cells grown without matrix. Firstly, there was no toxic effect observed with saporin treatments alone. While none of the ECM pretreatments affected cell attachment, bFGF-SAP at a 100 nM concentration inhibited cell proliferation (FIG. 6a). In contrast, a 20 nM bFGF-SAP pretreatment of the ECM had a proliferative effect similar to that observed with b-FGF (FIG. 6b). The results in FIG. 5 show the BEL cells that are located at the edge of the posterior lens capsule pre-incubated with 100 nM bFGF-SAP (LC on the photography). No cells are visible on the posterior capsule, but cells grow up to confluency on the Petri dish (PD on the photography) outside the LC. The characteristic morphological changers that accompany stimulation (elongation, reduction of the cell size) were noticed for cells grown on the plastic dish but in contact with the LC. FIG. 5 (A and B) shows the typical appearance of sparse cells grown on LIC pretreated with 100 nM bFGF-SAP and FIG. 5D shows typical appearance of cells grown on LC pretreated with basic FGF. BEL cells reached confluency on control LC (FIG. 5F) and on LC pretreated with 100 nM saporin (FIG. 5E).

Time course of bFGF-SAP toxic effect

Figure 7:
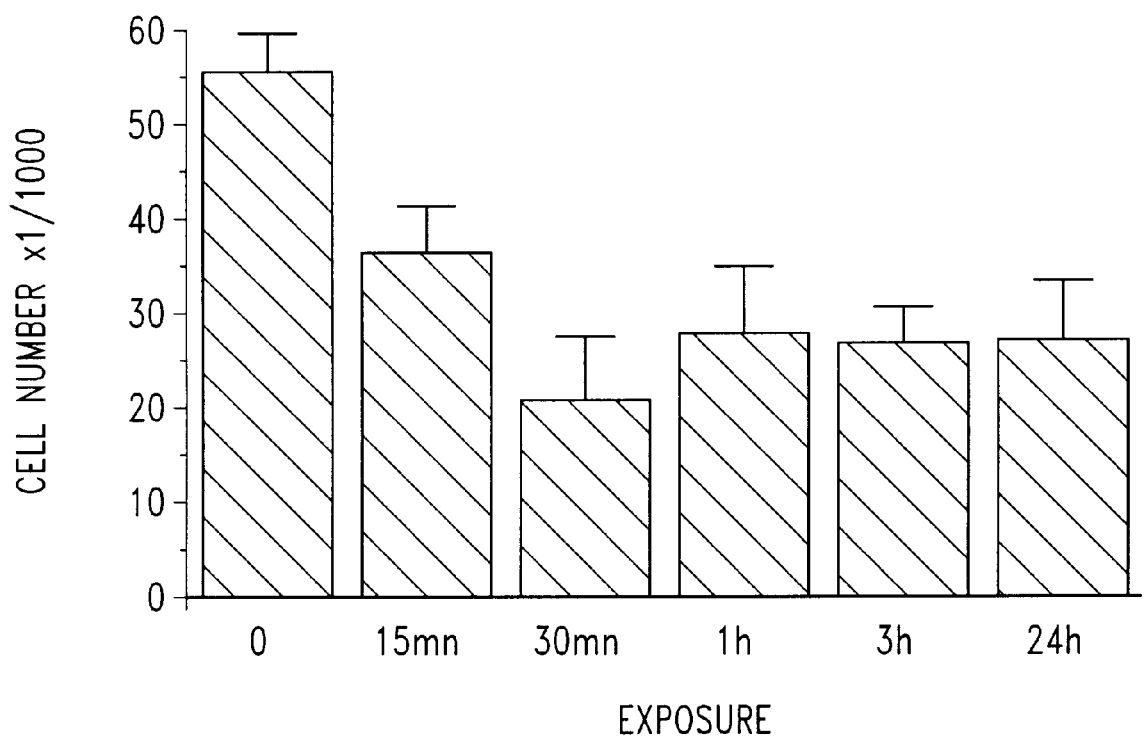
FIG. 7 shows the time course of 1 nM bFGF-SAP effects upon BEL cell proliferation. The cells were exposed (during the exponential growth phase) to 1 nM bFGF-SAP during the times indicated, and cell numbers were determined 4 days after the beginning of the exposure (T=0) (mean of three experiments).
Figure 8A:
FIG. 8A: control cells
Figure 8B:
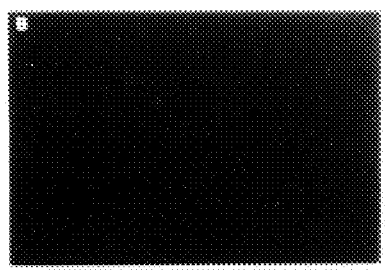
FIG. 8B: bFGF-SAP treated cells incubated with rabbit non-immune serum. X 110.
Figure 8C:
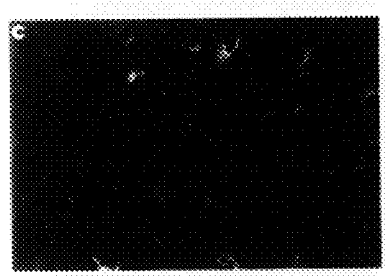
FIG. 8C: control cells incubated with anti-saporin antibody. X43.
Figure 8D:
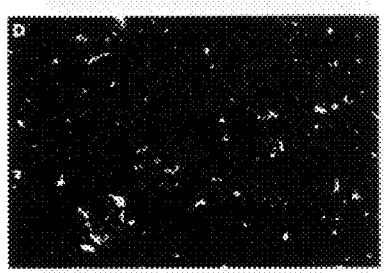
FIG. 8D: bFGF-SAP treated cells incubated with anti-saporin antibody. X43.
Figure 8E:
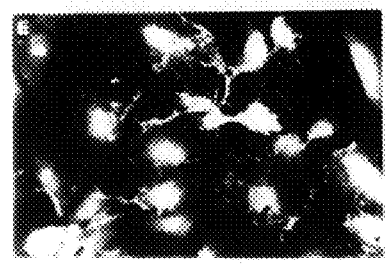
FIGS. 8E and 8F: bFGF-SAP treated cells, permeabilized with Triton X100 and incubated with anti-saporin antibody. X110 and X275.
Figure 8F:
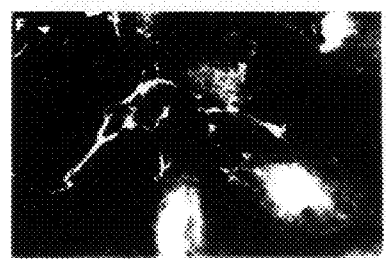
Figure 9A:
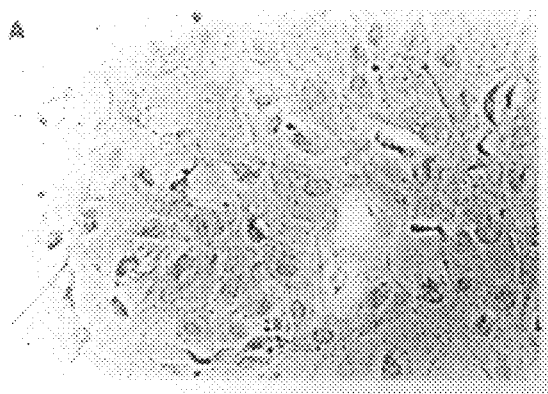
FIG. 9 shows the localization of bFGF-SAP conjugate on extracellular material produced by bFGF-SAP treated cells: analogy between the extracellular staining with anti-saporin antibody FIG. 9B and the staining with anti-fibronectin antibody FIG. 9C. X65.
Figure 9B:
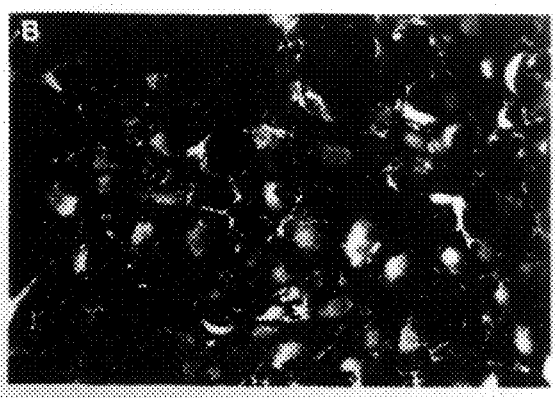
Figure 9C:
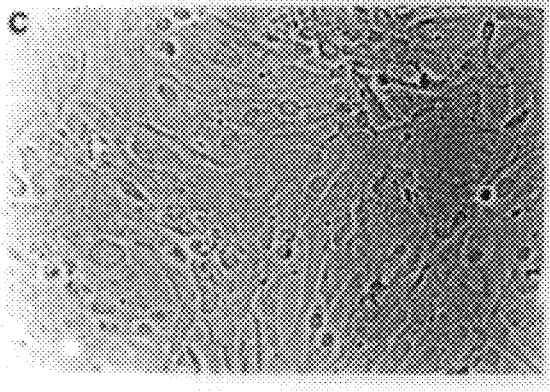
Figure 9D:
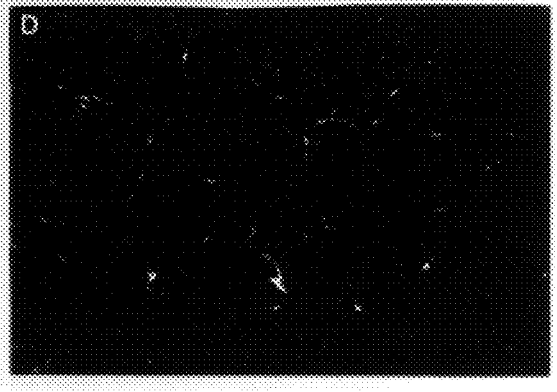

As shown in FIG. 7, a brief exposure (15 mn) of the BEL cells to 1 nM bFGF-SAP had an inhibitory effect on cell proliferation as measured 4 days later. The maximum inhibitory effect was reached with a 30 mn exposure. This is in agreement with the results of Lappi et al. (1991), that established toxic effect to BHK cells after a 15 mn incubation. However in that experiment increased incubation time to six hours increased bFGF-SAP cytotoxicity.

Immunolocalization of bFGF-SAP

A specific staining for immunoreactive saporin was observed on unpermeabilized cells and inside cells permeabilized with Triton X 100 (FIG. 8) when they were treated for 15 mn with bFGF-SAP. This staining pattern slowly decreased when the cells were examined 24 and 48 h after the initial 15 mn exposure (results not shown). The extracellular staining was similar to the pattern observed with antifibronectin antibodies (FIG. 9).

EXAMPLE 2

Cataract surgery was performed on the eyes of rabbits. The anterior part of the lens and the nucleus of the lens were removed in each case. 100 µl of solution containing doses of bFGF-SAP from 20 to 500 nM were injected into the anterior chamber of the eyes. The eyes were then closed.

No damage was observed to the corneal endothelium. Slight inflammatory reactions occurred in the anterior chamber of the eyes. In most cases, however, the reaction was less than in the eye of a control rabbit to which bFGP-SAP had not been administered. No proliferation of epithelial lens cells was observed.

I claim:

1. A lens implant, comprising a lens implant and a conjugate, said conjugate comprising a cytotoxic agent and a polypeptide reactive with a fibroblast growth factor receptor, wherein the conjugate is provided on the surface of the lens.

2. The implant of claim 1 that is coated with heparin prior to adsorption of the conjugate.

3. A composition formulated for use in inhibiting proliferation of epithelial lens cells in the eye of a patient, comprising an effective amount of a cytotoxic conjugate, wherein:

the cytotoxic conjugate comprises a cytotoxic agent and a polypeptide reactive with a fibroblast growth factor receptor;

the composition is formulated for local application to a posterior lens capsule; and the amount is effective for inhibiting proliferation of epithelial lens cells in the eye and preventing opacification of the posterior lens capsule following extracapsular cataract surgery.

4. The composition of claim 3, further comprising a product carrying polyanion charges for stabilizing the conjugate.

5. The composition of claim 3 or 4, wherein the effective amount is a concentration of the conjugate from 50 to 1000 nM in a volume of from 50 to 200 µl.

6. The composition of claim 5, wherein the concentration provides a dosage of the cytotoxic conjugate of from 100 to 500 nM in a volume of from 50 to 200 µl.

7. A method of inhibiting proliferation of epithelial lens cells, comprising, inserting a lens implant into an empty lens capsule of a patient, wherein a conjugate comprising a cytotoxic agent and a polypeptide reactive with a fibroblast growth factor (FGF) receptor is provided on a surface of the lens implant, and wherein the conjugate inhibits the proliferation of epithelial lens cells.

8. The method of claim 7, wherein the FGF is basic FGF and the cytotoxic agent is saporin.

9. The method of claim 7, wherein the polypeptide reactive with a FGF receptor is an FGF.

10. The method of claim 9, wherein the FGF is basic FGF.

11. The method of claim 7, wherein the cytotoxic agent is a ribosome-inactivating protein.

12. The method of claim 11, wherein the ribosome-inactivating protein is a type 1 ribosome-inactivating protein.

13. The method of claim 12, wherein the type 1 ribosome-inactivating protein is saporin.

14. A method of treating secondary lens clouding following extracapsular cataract surgery comprising, administering a lens implant to the eye of a patient, wherein a conjugate comprising a cytotoxic agent and a polypeptide reactive with a fibroblast growth factor (FGF) receptor is provided on a surface of the lens implant, and wherein the conjugate prevents secondary lens clouding.

* * * * *